(12) United States Patent
Stark et al.

(10) Patent No.: US 6,371,123 B1
(45) Date of Patent: *Apr. 16, 2002

(54) SYSTEM FOR ORTHOPEDIC TREATMENT PROTOCOL AND METHOD OF USE THEREOF

(75) Inventors: John G. Stark, Minnetonka; Duane Oyen, Maple Grove; Timothy J. B. Hanson, Plymouth; Timothy Tracey, Wayzata; Steven Backes, Minneapolis; Gary Manninen, Maple Grove, all of MN (US)

(73) Assignee: IZEX Technology, Inc., Golden Valley, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/329,880

(22) Filed: Jun. 11, 1999

(51) Int. Cl.[7] .................................... A61B 19/00
(52) U.S. Cl. .................... 128/898; 128/897; 128/920; 600/300; 600/595; 601/23
(58) Field of Search ............................ 128/898, 897, 128/920, 923; 600/300, 587, 595; 340/573.1; 432/262; 601/23, 33

(56) References Cited

U.S. PATENT DOCUMENTS

| | | | | |
|---|---|---|---|---|
| 5,052,375 A | * | 10/1991 | Stark et al. | 600/595 |
| 5,368,546 A | * | 11/1994 | Stark et al. | 601/34 |
| 5,484,389 A | * | 1/1996 | Stark et al. | 601/34 |
| 5,823,975 A | * | 10/1998 | Stark et al. | 600/595 |

* cited by examiner

Primary Examiner—Dinh X. Nguyen
(74) Attorney, Agent, or Firm—Patterson, Thuente, Skaar & Christensen, P.A.; Peter S. Dardi

(57) ABSTRACT

A process for treating orthopedic injuries including the steps of presenting a set of treatment protocols; approving a treatment protocol from among the presented set of treatment protocols; capturing information identifying the approved treatment protocol from among the set of presented protocols; and generating information from the captured information into a form compatible with a handheld computer adapted for connection to an orthopedic sensor system. The generated information includes parameters of the identified approved treatment protocol. The process may also include the steps of basing the presented set of treatment protocols upon a database of historic patients, orthopedic injuries, treatment protocols and outcomes, and retaining information about the current patient, the patients injury, treatment protocol and outcome. A system for treating orthopedic injuries with a historic database on a central computer and a handheld computer attached to a sensor system. The handheld computer has formatted treatment protocol parameters originating in the historic database and mediates treatment of the orthopedic injury.

39 Claims, 4 Drawing Sheets

SYSTEM FOR ORTHOPEDIC TREATMENT PROTOCOL AND METHOD OF USE THEREOF

BACKGROUND OF THE INVENTION

Field of Invention

The present invention relates to orthopedic treatment processes and, in particular, the present invention relates to preparing orthopedic treatment protocols used in conjunction with computerized or digitalized orthopedic treatment devices.

Orthopedic treatment historically involved a physician examining and diagnosing an orthopedic injury in a patient, prescribing a treatment protocol of activities or exercises for the patient to follow in order to facilitate healing, and subsequent re-examination to assess patient progress. Additionally, the patient was traditionally guided and assisted in following the prescribed treatment protocol by trained medical professionals, such as physical therapists, who could inform and advise the attending physician concerning patient compliance with the protocol and communicate and assist with the patient to provide desired activity details and elicit patient response. The traditional treatment path often included either hospitalization or patient visits at a physical therapy facility.

In modern times, financial pressure upon the medical arts and the surrounding medical industry has increased the number of patients each physician must treat and reduced the rate of hospitalization and tendency to employ physical therapy facilities, as well as reduced the direct supervision of the patient activities by the physical therapist. Computerized devices have been developed that at least partially substitute for the physical therapist contact, and yet monitor patient activities under a treatment protocol. One particularly innovative device system, the IZEX sensor-instrumented orthosis and associated Smart IDEA™ computer/conununicator, not only replace much of the physical therapist's function of (1) advising and instructing the patient and (2) advising the attending physician of patient compliance, but also allow an improved measuring and monitoring of patient rehabilitation activities and exercise parameters, such as effort exerted in rehabilitation exercises or stress applied to the orthopedic injury. This improved monitoring enables exploitation of a long observed and literature documented phenomenon of improved recovery in response to appropriately applied exercises to orthopedic injuries. The topic of accelerated and improved recovery through the use of controlled biofeedback based rehabilitation has been reviewed extensively by one of the present inventors in patents U.S. Pat. No. 5,052,375; U.S. Pat. No. 5,368,546; U.S. Pat. No. 5,484,389; and U.S. Pat. No. 5,823,975, and the entire disclosures of these patents are incorporated herein by reference.

The ultimate goal of efficiency and optimal and accelerated recovery outcomes still remains elusive, however, since the utilization of the IZEX™ orthosis brace system and Smart IDEA™ computer/communicator continues to rely upon physician examination, diagnosis and prescription of a treatment protocol for the injured patient. The physician may not readily know nor have available information concerning the optimal treatment protocol for an accurately diagnosed injury. It would be a significant advance in orthopedic treatment if a physician or other treatment professional could be rapidly advised concerning optimal treatment information based upon up-to-date experiential outcomes of similar treated injuries. It would also be a significant advance if the physician or treatment professional could leverage their own expertise and their colleagues' most recent knowledge to appropriately modify and adapt previously successful protocols to fit a new patient. It would also be a significant advance if the protocol could be installed in a handheld computer (monitoring device/computer/communicator) device with ease and efficiency. Additionally, it would be a significant advance to allow modification, particularly real-time modification, of rehabilitation exercise protocols by a user or in response to a user request, with such modification being limited by reasonable constraints. The following invention provides such advances to the orthopedic arts.

BRIEF DESCRIPTION OF THE FIGURES AND APPENDICES

Figure 1:
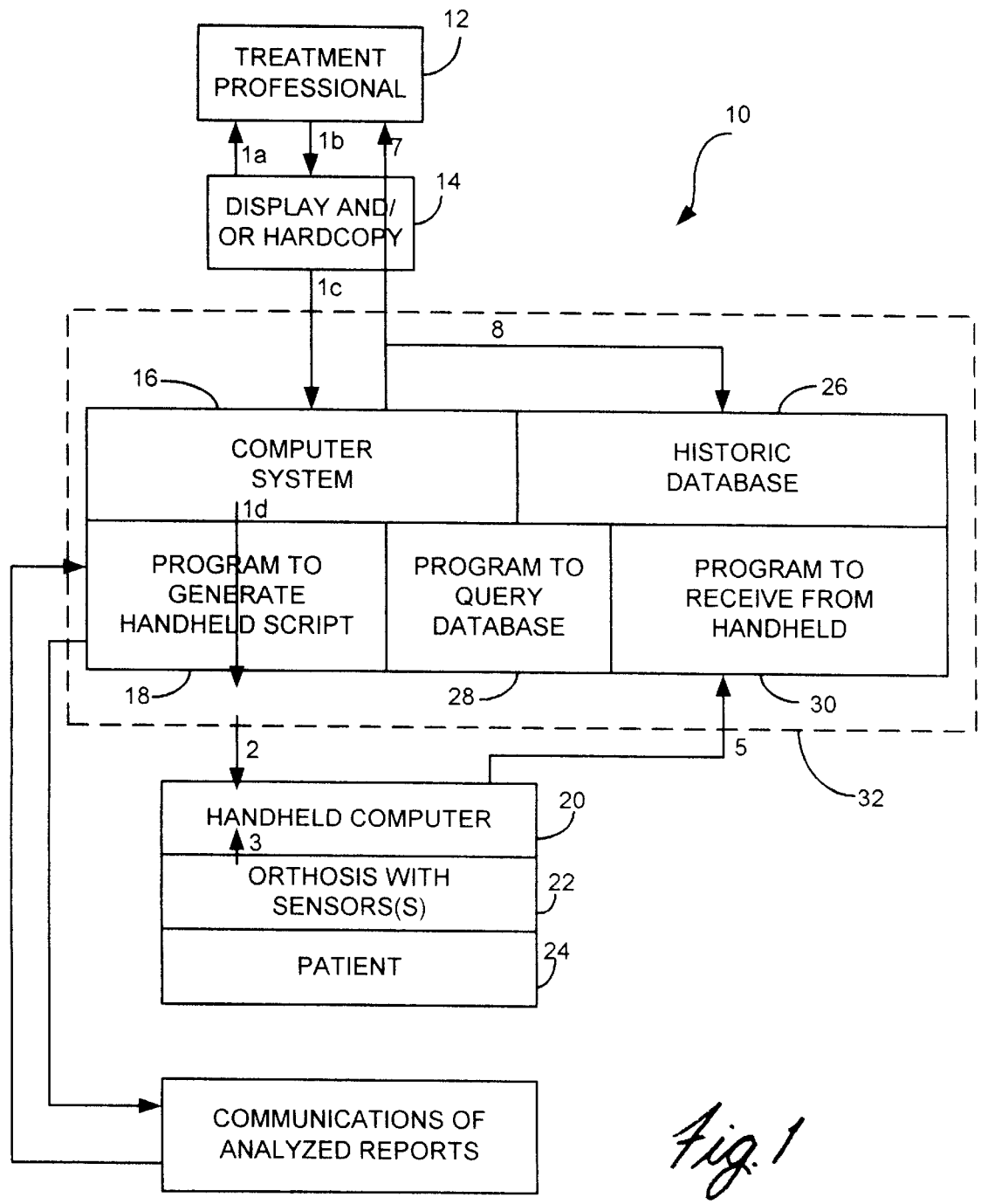
FIG. 1 is a schematic diagram of the relationship between participants and equipment used in the process according to the present invention.

Appendix A is a recorded data format for use in the present invention;

Appendix B is a protocol structure definition for use in the present invention;

Appendix C is another view of various embodiments of an orthopedic treatment system/process/&method of the present invention; and Appendix D is another schematic view of the data handing, flow, components and approaches of the present invention.

SUMMARY OF THE INVENTION

The present invention, in a first embodiment, is a process for treating an orthopedic injury. The inventive process involves performing a number of steps to generate information about a prescribed protocol for treating the orthopedic injury of a patient. Such generated information may be in the form of a script, which may be used in a handheld computer and orthosis device combination to treat an orthopedic injury. The process steps include:

a.) Presentation of a set of treatment protocols. The presented set of protocols includes at least one treatment protocol. The presentation might be on a display screen or a paper printout or similar hardcopy or both. (as represented for example in FIG. 2 at "1a")

b.) Approval of a treatment protocol from among the presented set of treatment protocols. This step is undertaken by a treatment professional using professional judgement and, generally, the approval is made in light of further information about the treatment protocol which is being approved. (as represented for example in FIG. 2 at "1b")

c.) Capture information identifying the approved treatment protocol of the set of presented protocols. (as represented for example in FIG. 2 at "1c") and, d.) Generate information from the captured information into a form compatible with a handheld computer adapted for connection to an orthopedic sensor system, wherein the generated information includes parameters of the identified approved treatment protocol. (as represented for example in FIG. 2 at "1*d*")

Additionally the method may include e.) communication from the portable monitoring and communication device of information concerning interactions, communication exchange and/or patient exercise; and f.) modification of the treatment protocol; and g.) monitoring the new protocol.

The present invention includes a number of further embodiments. One particularly notable embodiment involves a database of historic information of earlier patients, their injuries, their actual treatments protocols as performed, and resulting outcomes and a communications and data method to connect the two optimizing functions together. Information is accumulated in such a database during the process of certain embodiments and information from the database is made available and utilized in other embodiments.

The present invention in another embodiment is a system for treating an orthopedic injury. The system includes a handheld computer adapted for connection to an orthopedic sensor system, a central computer including historic database of orthopedic injuries, patient characteristics, treatment protocols and outcomes. With the system, the central computer is queried to present a set of treatment protocols to a treatment professional. The treatment professional approves a treatment protocol of the set and the system generates formatted parameters corresponding to the approved treatment protocol for installation in the handheld computer. Once installed with such parameters, the handheld computer can mediate the approved treatment protocol when it is connected to the orthopedic sensor sytem. The system further includes monitoring performance of the treatment protocol and updating the historic database with the monitored performance parameters. The system further includes modification of the formatted treatment protocol parameters in real-time in response to updates to the historic database. Data which is transmitted to the central computer can be analysed against other databases and more channels and sent on for other analysis. When the data is sent (COMMUNICATED) secure communication may be optionally employed.

DETAILED DISCLOSURE OF PREFERRED EMBODIMENTS

Figure 2:
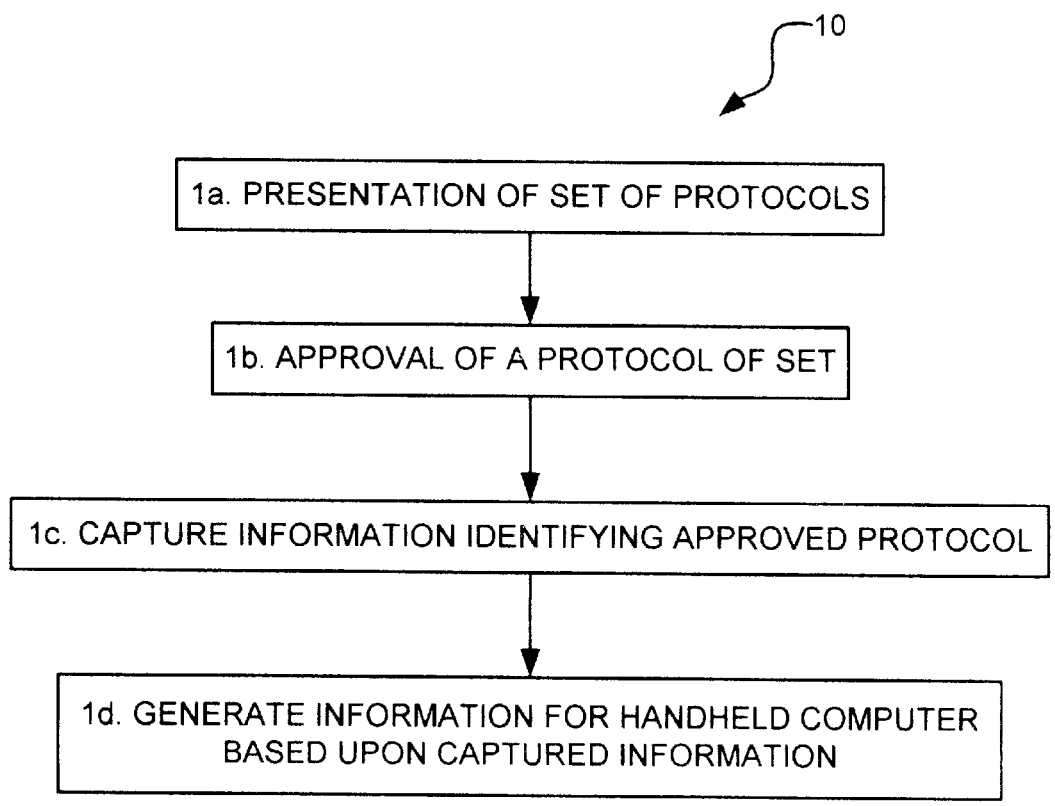
FIG. 2 is a schematic of the steps included in the process of the present invention.

The present invention, in a first embodiment, is a process for treating an orthopedic injury of a patient under care of a treatment professional. The process is illustrated in FIG. 2 at 10 and FIG. 1 is provided to depict relationships between participants and equipment in carrying out the inventive process 10. The process 10 includes the following steps:

First, a set of treatment protocols is presented "1*a*"to the treatment professional 12. The set of treatment protocols to be presented includes at least one treatment protocol but optionally and often includes a plurality of treatment protocols which relate to the patient's orthopedic injury. The presentation step may include, preferably, displaying the set as an image, preferably a set of images on a computer screen 14, such as a CRT screen or LCD screen, or may include providing a printed copy 14 of the presented set, or may provide both. The presentation may be graphical, textual or a mixture of graphical and textual. Additional information, again graphical, textual or mixed graphic and text may accompany the presentation, for example, in order to provide additional information about the protocol set or individual protocols of the set. Examples of additional information which may be presented to the treatment professional are historic, statistical, or predicted outcomes. As with the earlier mentioned presentation of the set, such additional information may be presented textually or as a graphic, including a color attribute of a graphic or text being presented.

To explain further the step of presentation of the set of treatments protocols to the treatment profession, consider some preferred embodiments and a few illustrative examples. One preferred presentation includes graphical figures or icons on the screen, wherein the graphical figures are animated such that they facilitate rapid comprehension of the form of exercise motion being presented. For example, in the situation of an orthopedic injury associated with a patient's knee, the treatment professional might be presented with a screen display having a set of animated graphical figures representing possible treatment protocols involving the patient's knee performing bending exercises. This may be accomplished by including animated movement of either a set of stick-characters' legs with knees bending or a more realistic depiction of side views of legs having bendable or bending knees. In such an animated graphical representation, the degree of bending of each of the depicted animated knees is presented as an animated graphic by a series of screens with incremental changes of screen positions of one or both of the portions of the leg adjacent the knee. The sequential display of such screens conveys an impression of motion, in the form of knee bending, to the treatment professional. An arcuate arrow using the knee as an axis or pivot point, might show limits of range of motion for one or more of the bending knees. Textual information might also be simultaneously presented, for example, the patient's name or similar identification might show on the screen as well as the degree of motion being depicted by the arcuate arrow. Additionally, sounds, such as oral descriptions of the exercise treatments protocols or associated parameters, including especially patient directed voice comments, might be presented or made available for presentation with the set, or individual treatment protocols of the set.

It should be recognized that the ability to directly utilize sound files for patient directed voice comments requires inclusion of a speaker in the hand-held computer, however, patient directed voice comments alternatively might be provided as separate analog or digital recordings, for example, as cassette tapes or compact disk recordings and the patient directed to listen by visual information provided by the hand-held computer. Moreover, computerized video files or the availability to call up a designated computerized video file, may also be included in the presentation. As with sound files, the efficiency of presentations including video files is dependent on the availability of sufficient communications "bandwidth." However, both the treatment professional and patient benefit from such richer or expandable presentation of the set by rapidly and efficiently comprehending and considering choices in available and appropriate treatment protocol for the patient.

In a second step, a treatment protocol from amongst the presented set of treatment protocols is approved by the treatment professional "1*b*". In a preferred embodiment, the approval step includes highlighting a graphical representation of the particular treatment protocol selected for approval by the treatment professional. This step may be performed efficiently by employing a mouse or similar pointing device to move a cursor in a graphical user interface (GUI) and clicking or double clicking to highlight and approve the selected treatment protocol. Alternatively, in a textual or mixed textual and graphical interface, each protocol, including each of any number of predesigned, pre-entered protocols has a protocol identifier such as a number or letter or name associated with the treatment protocol. The protocol identifier for the protocol which is to be approved is input from a keyboard and entered. Other alternative approval steps may involve a touch screen, lightpen, or voice input. In a most preferred embodiment, the approving step includes causing a visual change to the presentation upon a screen display and then inputting an "enter" command, either by keyboard, by a mouse button click, by a voice command of the treatment professional, or by touching the screen of a touch sensitive screen display.

Next, the treatment professional's approval of a particular treatment protocol of the presented set is captured "1c". That is, information is captured which identifies the approved treatment protocol of the set of presented protocols. In a first embodiment, the captured identification is less than the entire information detailing the approved treatment protocol, but may be used to retrieve or regenerate the entire information; in a second embodiment, the captured information includes the entire information detailing the treatment protocol. To accomplish the capture, a computer program is provided. A computer system 16 is present, and may be one or more computers; optimally if separate computers, the separate computers are linked, for example on an intranet or on the Internet 32. Other programs 28 and 30 are present in the computer system 16 as will be discussed subsequently. Additionally, a historic database 26, also discussed subsequently, is present in a memory/storage device and available to the computer system 16.

In the next step "1d", information is generated from the captured information into a form compatible with a handheld computer adapted for connection to an orthopedic sensor system. The generated information includes parameters and details of the identified approved treatment protocol. This step might be understood in terms of a translation of at least a portion of the information used in the presentation set or represented by the presentation set into a script usable by a handheld device such as a SMART IDEA™ device available from IZEX Technologies, Inc, Golden Valley Minn. The recorded data format and protocol structure definition employed for data recording, storage, and subsequent communication with the SMART IDEA device, are provided in Appendices A and B respectively, and together are examples of a suitable script for generation by this step. Example of other handheld computer devices which may be adapted to serve in the role of the handheld computer are the PALM PILOT brand series and PALM brand series of handheld personal computers available from the 3COM division of U.S. Robotics Corporation, the NINO brand handheld computer of Phillips Electronics, the JORNADA brand of handheld computers of Hewlett Packard. The SMART IDEA™ device 20 is connectable to a compatible orthosis device 22 on the patient 24 to be treated, such orthosis devices have been previously disclosed in U.S. Pat. No. 5,052,375, the entire disclosure of which is hereby incorporated by reference. An orthosis of this type includes sensors or a system of sensors. When the sensor system of such a device is connected to a suitable handheld computer, the step of monitoring may be accomplished by receiving a signal from a sensor or a system of sensors. The process may also be employed with sensors directly attached to the body, (instead of mounted upon and in conjunction with an orthosis,) which communicate by signaling through a connection to a handheld computer, such as a SMART IDEA™ device.

Figure 3:
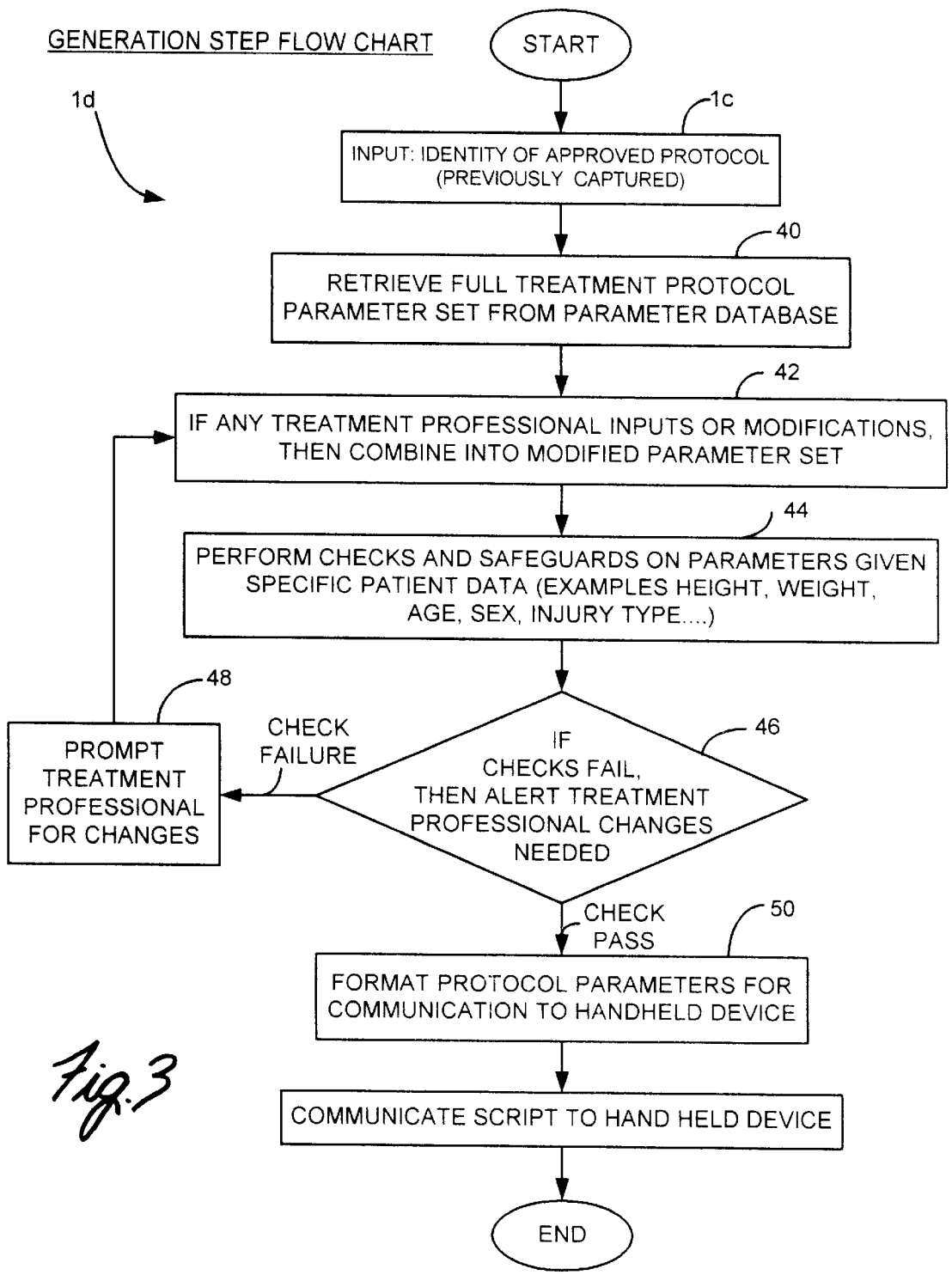
FIG. 3 is a schematic of details of the generation step of FIG. 2.
Figure 4:
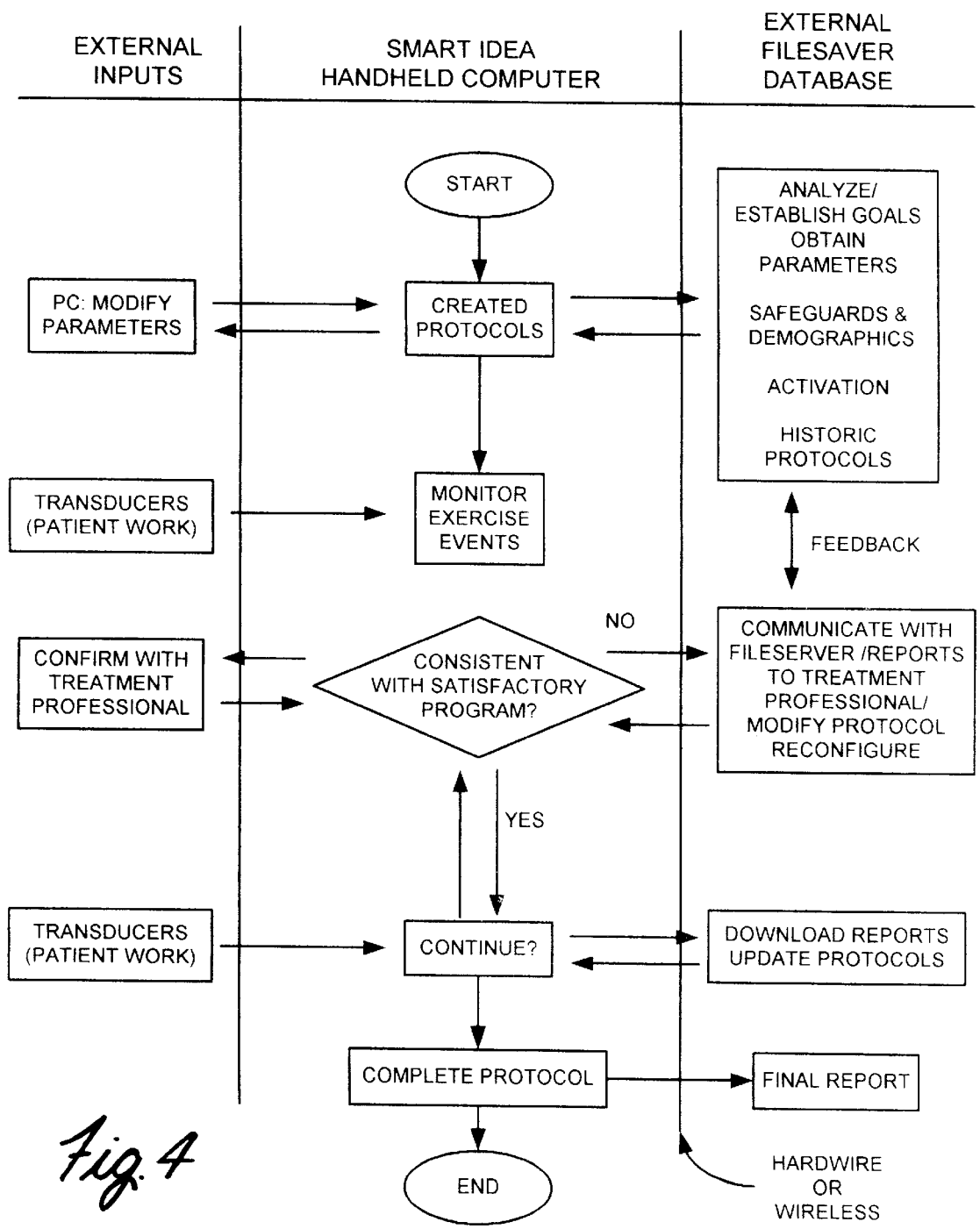
FIG. 4 is a another schematic of the inter-rationships of the systems of the present invention, especially between external inputs (left column), the handheld portable computer, for example an IZEX brand SMART IDEA (center column), and an external fileserver with a database (right column.)

The generation step is shown in more detail in FIG. 3 at "1d". The input is the captured identification information resulting from earlier step "1c". The program 18 begins with a retrieval 40 of the full set of protocol parameters for the identified protocol from a protocol parameters database. The protocol parameters database, in a preferred embodiment, is, or is a subpart of, historic database 26. Next 42, the program 18 looks for any modifications or other input from the treatment professional 12. Possible modifications and input are discussed subsequently but might include a recording of voice instructions to the patient 24. If any modifications or other input are present, it is combined with the parameters from the database to form a modified or augmented treatment protocol. The protocol parameters, possibly modified, are then checked 44 against a set of standard checks or safeguards. The source of the safeguard information may be based upon information stored in the historic database 26 or a separate database, isolated from the historic database 26. Basis of safeguarding information against which the parameters may be checked are statistical norms, desired outcome information, biomechanical safety data, parameter interrelationships, and information generated by querying the database, for example by program 28, to determine whether a simulated outcome result is consistent with the predicted outcome previously presented to the treatment professional 12. Yet another safeguard involved checking to see whether the protocol parameters are consistent with the handheld computer 20 which will be used. This safeguard becomes more significant should more than one model or type of handheld computer 20 be present in an installed base of handheld computers and variations exist between the capabilities of the handheld computers 20. For example, if the protocol were supplying a patient voice communication file or initiator of such a file to a handheld computer 20 which is incapable of playing the file, then the check would generate a prompt to the treatment professional to substitute a different instruction set, different equipment, or augment the sound limited handheld computer 20 with a compact disk player which can be controlled by the handheld computer 20.

If the safeguard checking fails 46, then the program 18 preferably provides for a prompt 48 of the treatment professional 12 to provide different modifications. The prompt 48 is made by a presentation to the treatment professional 12 that the modification is unacceptable. Newly provided modifications, if any, are then recombined with the original full treatment protocol parameter set 40 to reattempt to create a modified treat protocol parameter set 42. If the check passes, then the parameter set is formatted 50 consistent with the script acceptable to the handheld computer 20. Appendices A and B represent a recorded data format and protocol structure definition consistent and compatible with a SMART IDEA device, and may be used in a process according to a preferred embodiment of the present invention.

Having generated or translated the treatment protocol information into an appropriate form, the process has resulted in production of a treatment protocol script by an attending treatment professional in an efficient manner. The treatment protocol script is available and useful in treating the patient's orthopedic injury. The most usefull basic process of the present invention may be employed, expanded, and incorporated into several inventive processes, as summarized below.

In one preferred embodiment of the present invention, the process further includes the step of loading 2 the generated information in the handheld computer 20. Continuing the application involving the SMART IDEA™ device, the information, in the form of a script would be loaded into the SMART IDEA™ device. The SMART IDEA™ device would then be available for connection to an orthosis which may be attached or pre-attached to the patient. In some situations, the loading may be by direct connection to the treatment professional's computer, for example, through an RS-232 or PC1 cable connection. In other situations, the two computers may separated a considerable distance and the script communicated over telephone lines through modem connections. In a most preferred embodiment, the communication sending the script to load the SMART IDEA™ device would be via the Internet 32, an intranet, or other multi-media communication network.

In another preferred embodiment, the process further includes the step of monitoring 3 patient activity relative to the approved treatment protocol and storing data resulting from the monitoring in the handheld computer. Continuing the explanation utilizing the SMART IDEA™ device, the patient's exercise activities, most preferably initiated in response to a patient signal originating from the SMART IDEA™ device, are monitored and stored in the SMART IDEA™ device. The SMART IDEA™ device includes memory elements allowing for such storage of data.

In yet another preferred embodiment, the process continues by adding the optional step of processing the stored data from the monitoring, for determination of compliance relative to the approved treatment protocol. This embodiment, involving what may be termed "compliance processing" is within the data processing capabilities of a SMART IDEA™ device.

In still another embodiment, the process further includes the step of communicating information 5 concerning the stored monitoring data to a central computer. Alternatively, the present invention is embodied in a process including the further step of communicating the processed stored data from the monitoring for compliance relative to the approved treatment protocol to a central computer. These embodiments may be understood as communicating raw data or processed data from the SMART IDEA™ device to a central computer, respectively. In a preferred embodiment of either of these, the embodiments may communicate their respective data from the SMART IDEA™ device to a central computer via the Internet or an intranet. The communication might also involve a combination of raw and processed data. If raw data is communicated, then the process may further include the step of processing the communicated information at the central computer. Data processed prior to communication may also be further processed or reduced at the central computer.

The data received at the central computer is available for presentation 7 and preferably includes processed patient monitoring and compliance information. As with the earlier presentation of the set, the data may be presented, either on screen or in printed form or both; and the presented data may be graphically, textually or a combination of both. The data may also be used to update 8 a historic database 26 with the processed patient compliance information. Use of the data for presentation in order to allow review by a treatment professional or in updating a historic database are not mutually exclusive, and in a most preferred embodiment, both steps are available and utilized in a treatment process according to the present invention. It should be understood, that the reviewing treatment professional and the treatment professional involved in the earlier approval step are not necessarily the same individual. Presented data and updated data may additionally be communicated and employed for other uses, such as for example, governmental compliance, insurance purposes, and/or financial reimbursement or employment records. Methods of limiting access to the data in the central computer for confidentiality purposes or financial purposes are, of course well known, and might include passwords or, in the case of intranets and private access networks, may also include call back modems as security enhancements.

In the process of the present invention, the treatment protocol information resulting from the script generation step may include parameters such as an exercise identification parameter, an exercise replication parameter, and an exercise initiation timing parameter. These parameters serve to define at least part of the treatment protocol approved from the presented set of treatment protocols.

Consistent with capabilities of a handheld computer such as, by way of example, the SMART IDEA™ device, the handheld computer may also include patient signaling capabilities selected from the group consisting of audible signaling, visual signaling, and tactile signaling. Similarly, the handheld computer may include input capabilities selected f rom the group consisting of RS-232 input, sensor signal input, USB input, modem input, keyboard input, audible input, light input, and Ethernet input. Moreover, the handheld computer may include output capabilities selected from the group consisting of RS-232 output, USB output, parallel port output, light output, textual, graphical, audible output, Ethernet input, and tactile output.

The present invention's usefulness may be further understood in view of some particularly preferred embodiments. In one such embodiment, the presented set of treatment protocols is based upon information gleaned from a database 26. The database 26 includes a plurality of historic treatment protocol records, the records including fields populated by parameter data for patient characteristics, orthopedic injury, actual treatment protocol followed by the patient, and historic outcome. By "historic treatment protocols" herein is meant herein actual, accomplished and monitored treatment protocols; and by "historic outcomes" herein is meant the actual, observed recovery or extent of recovery resulting from such "historic treatment protocols." Additionally, in a most particularly preferred embodiment, the database 26 further includes parameter data selected from the group of characteristics consisting of patient physical characteristics, patient psychological characteristics, and prescribed protocol provided to the patient. In one variation of this treatment process, the presented set of treatment protocols is based upon statistical analysis of data base records. In another variation, the presented set of treatment protocols includes at least portions of one record of the database. That is, in the first variation the treatment professional is presented with statistical information, such as summaries, means, averages, medians or the like; in the second variation, the treatment professional is presented with at least portions of one or more records presented, where the records are in effect individual case histories. Most preferably, the presented case history records are of patients with similar characteristics and similar injuries to the patient about be treated.

In one embodiment, the treatment professional 12 has the initial opportunity to query the database 26 with at least some parameters characteristic of the current patient 24 and the current patient's orthopedic injury. A computer program 28 is present in the computer system 16 to query the database 26. This allows the database 26 to be searched for similar case histories in the form of historic records of treatment protocols and outcomes. Alternatively, the query might be used to return statistical information relevant to the patient 24. In an extension of these treatment processes, the treatment professional 12 may modify the initial query, to increase or decrease the number of returned records for presentation. Additionally, the historic database 26 may allow queries for predicting the likely outcome of a treatment protocol for a patient 24 with a particular set of characteristics and a particular orthopedic injury. Using this approach, a treatment professional 12 can rapidly investigate the efficacy of a range of possible treatment protocols which they might envision for the patient 24 with the orthopedic injury. Additionally, once at least one treatment protocol is presented, the treatment professional 12 may either modify the presented protocol or the patient characteristics and either re-query the database 26 for likely outcomes or proceed to approve the protocol. In this process step, it is further provided that the treatment professional may utilize the query program and historical database as part of the treatment system of this invention to simulate an evaluation of a treatment protocol under consideration for a particular patient, then re-modify the treatment protocol based upon the simnulation outputs.

It is also part of the present invention that the treatment professional may, in modifying the treatment protocol, select from various pre-recorded sound files, one or more patient directed voice comments, or record one or more individualized i.e. customized voice comments to the patient. As mentioned previously, the sound files may be played later for the patient as part of the treatment protocol or conditionally played as part of the treatment protocol. If the hand-held computer 20 includes the capability to play sound files, then the files are played via the hand-held computer 20. Alternatively, the handheld computer 20 may signal the patient to play the recorded file, for example, by displaying a message on an LCD screen for the patient to do an added motivational or instructional task such as "Listen side #2 cassette recording!" to cause the patient to play an analog cassette recording of reproduced sound selected by or custom recorded by the treatment professional. In another variation of this aspect of the process, the sound files may be provided to the patient as a set of sound files on a device in communication with the hand-held computer 20 such that the device is instructed to play a particular sound file. By way of example, this variation may involve a compact disc recording of one or more sound track files of patient directed comments and a communication link between the hand-held computer 20 and a compact disc player device, with the ability to be controlled by the hand-held computer. Such control might be by a direct wire communication connection or by an infared signal originated by the handheld computer 20. The compact disc may be recorded with generic patient directed voice comments or customized comments, such as the treatment professional's voice recording of custom instructions and or encouragement for the particular patient. In the case of custom instructions, treatment protocol modification step, further includes the treatment professional recording the customized patient instructions, and the generation step, described earlier, further includes the substep of recording the track onto a recordable or rewritable compact disc.

Once approved, the overall process may be continued to capture "1c" and then generate "1d" information for a handheld computer 20. The steps of modifying one or more treatment protocols of a presented set and re-presenting the modified set for availability to the approval step facilitates the treatment professional's ability to rapidly and efficiently prescribe a treatment protocol with a high degree of confidence.

Another preferred embodiment of the present invention includes the additional steps of programming review of the data received from the handheld computer 20 by the program 30 for compliance with the prescribed treatment protocol as well as for reconsideration of the effectiveness of the prescribed protocol relative to updates in the database since the treatment protocol was initially prescribed and loaded into the handheld computer. That is, it is entirely feasible that the updating of the historic database 26 with information from other patients, rather than the patient 24 being treated in this process, will suggest a modification of the treatment protocol. The newly suggested modification may be presented to the treatment professional or, alternatively, a new script automatically generated, communicated to and loaded into the handheld computer 20.

In another embodiment, failure of the patient 24 to comply with the treatment protocol may suggest a centrally generated modification, either with or without presentation and review by the treatment professional 12. Failure to comply may include under or over exercise which deviates from the treatment protocol.

In yet another embodiment, the script corresponding to the treatment protocol may further include conditional logic. In such an embodiment, the conditional logic may be used to provide the criterion for recognition by the remotely located handheld computer 20 of a failure of compliance by the patient 24 and the ability to alter the treatment protocol. Alternatively, the conditional logic may be used to provide criteria for recognition by the remotely located handheld computer 20 of meeting or satisfying the treatment goal set by the treatment professional as represented by the approved treatment protocol. The alteration need not be immediately communicated back to the central computer but might be saved for later communication.

In still another embodiment, the treatment protocol may include information to generate patient communication signals to alter the patient's perception of either the protocol's instructions or the urgency of the patient's compliance with the instructions. Such additional aspects of the information carried within the scripting being loaded into the handheld computer 20 can relieve the treatment professional of many time consuming and inefficient contacts with the patient 24 yet facilitate the patient's compliance.

For example, patient oral communication files, or parameters to cause patient oral communication files which are pre-installed on the hand-held computer, which might be played to a patient could be included with a treatment protocol or a modified treatment protocol. In particular, sounds, such as oral encouragement or descriptions of the patient exercise to be performed, most especially patient directed voice comments, such as "Keep going Bob; You are almost there!" might be available for inclusion in treatment protocols. The ability to modify the oral comments sound file is particularly useful with real-time modification for increasing patient compliance with an individual treatment protocols of the set.

Although the present invention has been described with reference to preferred embodiments, workers skilled in the art will recognize that changes may be made in form and detail without departing from the spirit and scope of the invention.

What is claimed is:

1. A process of treating an orthopedic injury, the process comprising the steps of:

a. presenting a set of treatment protocols, wherein the set of protocols includes at least one treatment protocol;

b. approving a treatment protocol from among the presented set of treatment protocols;

c. capturing information identifying the approved treatment protocol of the set of presented protocols; and d. generating information from the captured information into a form compatible with a handheld computer adapted for connection to an orthopedic sensor system, wherein the generated information includes parameters of the identified approved treatment protocol.

2. The process of claim 1 and further comprising the step of:

loading the generated information in the handheld computer.

3. The process of claim 2 and further comprising the step of:

monitoring patient activity relative to the approved treatment protocol and storing data resulting from the monitoring in the handheld computer.

4. The process of claim 3 and further comprising the steps of:

processing the stored data from the monitoring for compliance relative to the approved treatment protocol.

5. The process of claim 3 and further comprising the step of:

communicating information concerning the stored monitoring data to a central computer.

6. The process of claim 4 and further comprising the step of:

communicating the processed stored data from the monitoring for compliance relative to the approved treatment protocol to a central computer.

7. The process of claim 5 and further comprising the step of:

processing the communicated information at the central computer.

8. The process of claim 5 and further comprising the step of:

further processing the communicated information at the central computer.

9. The process of claim 7 and further comprising the step of:

presenting processed patient monitoring and compliance information.

10. The process of claim 7 and further comprising the step of:

updating a historic database with the processed patient compliance information.

11. The process of claim 1 and where in the step of presenting includes providing a screen display.

12. The process of claim 1 and wherein the step of presenting includes providing a printout.

13. The process of claim 1 and wherein the step of presenting includes representing a treatment protocol parameter as an image selected from the group of images consisting of textual representation, graphic representation, and combined textual and graphic representation.

14. The process of claim 11 and wherein the step of approving a treatment protocol includes the step of causing a visual change in the presented screen display.

15. The process of claim 14 and wherein the step of capturing includes the step of inputting an "enter" command subsequent to causing a visual change in the presented screen display.

16. The process of claim 1 and wherein the parameters of the generated information includes an exercise identification parameter, an exercise replication parameter, and an exercise initiation timing parameter, which parameters define at least part of the treatment protocol approved from the presented set of treatment protocols.

17. The process of claim 1 and wherein the handheld computer includes patient signaling capabilities selected from the group consisting of audible signaling, visual signaling, and tactile signaling.

18. The process of claim 1 and wherein the handheld computer includes input capabilities selected from the group consisting of RS-232 input, sensor signal input, USB input, modem input, keyboard input, audible input, light input, Ethernet input.

19. The process of claim 1 and wherein the handheld computer includes output capabilities selected from the group consisting of RS-232 output, USB output, parallel port output, light output, textual output, graphical output, audible output, Ethernet input, tactile output, and hardcopy printer output.

20. The process of claim 3 and wherein the step of monitoring includes receiving a signal from at least one sensor.

21. The process of claim 20 and wherein the sensor is mounted on an orthosis device attached to the patient.

22. The process of claim 20 and wherein the sensor is directly attached to the patient.

23. The process of claim 1 and wherein the presented set of treatment protocols is based upon information gleaned from a database, wherein the database includes a plurality of historic treatment protocol records, the records including fields populated by parameter data for patient characteristics, orthopedic injury characteristics, actual treatment protocol followed by the patient, and historic outcome.

24. The process of claim 23 and wherein the database further includes parameter data selected from the group of characteristics consisting of patient physical characteristics, patient psychological characteristics, and prescribed protocol provided to the patient.

25. The process of claim 23 and wherein the presented set of treatment protocols is based upon statistical analysis of database records.

26. The process of claim 24 and wherein the presented set of treatment protocols includes at least portions of one record of the database.

27. The process of claim 23 and wherein the step of presenting a set of treatment protocols based upon information is gleaned from the database is preceded by the step of:

querying the database such that the set of treatment protocols is presented in response to the query, the query including at least parameters characteristic of the orthopedic injury of the patient to be treated.

28. The process of claim 1 and further comprising the steps of:

modifying a first set of presented treatment protocols; and presenting the resulting modified set of treatment protocols for availability in the approving step.

29. The process of claim 23 and wherein the presentation includes predicted outcomes for at least one treatment protocol of the set, the predicted outcome based upon information derived from the historic database of treatment protocols.

30. The process of claim 1 and wherein the generated information includes information to cause voice comments to be played for a patient.

31. The process of claim 30 and wherein the information generated to cause voice comments is a sound file.

32. The process of claim 30 and wherein the voice comments are present as sound files in the handheld computer.

33. The process of claim 30 and wherein the voice comments are present as sound files in a separate device other than the handheld computer.

34. The process of claim 30 and wherein the voice comments are played conditionally depending upon processed information derived from the orthopedic sensor system.

35. The process of claim 30 and wherein the voice comments are a subset of a more extensive set of voice comments.

36. The process of claim 30 and wherein the voice comments are recorded by a treatment professional approving the treatment protocol as an adjunct to the protocol.

37. A system for treating an orthopedic injury, comprising:

a handheld computer adapted for connection to an orthopedic sensor system;

a central computer including historic database of orthopedic injuries, patient characteristics, treatment protocols and outcomes;

means to query the central computer to present a set of treatment protocols to a treatment professional;

means to approve a treatment protocol of the set; and, means to generate formatted parameters corresponding to the approved treatment protocol for installation the handheld computer, thereby allowing the handheld to mediate the approved treatment protocol when connected to the orthopedic sensor sytem.

38. The system of claim 37 and further comprising:

means to monitor performance of the treatment protocol and update the historic database with performance parameters.

39. The system of claim 38 and further comprising:

means to modify the formatted treatment protocol parameters in real-time in response to updates to the historic database.

* * * * *